(12) United States Patent
Nelson et al.

(10) Patent No.: US 9,545,421 B2
(45) Date of Patent: *Jan. 17, 2017

(54) NUCLEIC ACID DELIVERY VEHICLE AND USES THEREOF

(75) Inventors: John Richard Nelson, Clifton Park, NY (US); Timothy James Yosenick, Glenville, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 415 days.

This patent is subject to a terminal disclaimer.

(21) Appl. No.: 12/773,478

(22) Filed: May 4, 2010

(65) Prior Publication Data

US 2011/0274757 A1   Nov. 10, 2011

(51) Int. Cl.

| | | |
|---|---|---|
| A61K 9/14 | (2006.01) | |
| A61K 31/7105 | (2006.01) | |
| A61K 31/711 | (2006.01) | |
| A61K 39/00 | (2006.01) | |
| A61P 37/04 | (2006.01) | |
| A61K 9/16 | (2006.01) | |
| A61K 31/7088 | (2006.01) | |
| A61K 33/26 | (2006.01) | |
| A61K 45/06 | (2006.01) | |
| A61K 47/48 | (2006.01) | |
| A61K 9/00 | (2006.01) | |
| A61M 35/00 | (2006.01) | |

(52) U.S. Cl.
CPC ......... *A61K 31/7105* (2013.01); *A61K 9/1611* (2013.01); *A61K 31/7088* (2013.01); *A61K 31/711* (2013.01); *A61K 33/26* (2013.01); *A61K 45/06* (2013.01); *A61K 47/48861* (2013.01); *A61K 9/0019* (2013.01); *A61K 2039/53* (2013.01); *A61M 35/00* (2013.01)

(58) Field of Classification Search
None
See application file for complete search history.

(56) References Cited

U.S. PATENT DOCUMENTS

| | | | |
|---|---|---|---|
| 5,462,751 A | 10/1995 | Kossovsky et al. | |
| 6,972,013 B1 | 12/2005 | Zhang et al. | |
| 7,332,586 B2 | 2/2008 | Franzen et al. | |
| 2007/0178593 A1 | 8/2007 | Miller et al. | |
| 2008/0199529 A1 | 8/2008 | Franzen et al. | |
| 2008/0286366 A1 | 11/2008 | Fischer et al. | |

FOREIGN PATENT DOCUMENTS

| | | |
|---|---|---|
| EP | 0774974 B1 | 5/2002 |
| WO | 9639524 A1 | 12/1996 |
| WO | 2009047587 A1 | 4/2009 |

OTHER PUBLICATIONS

Yang, et al. (May 2007) "Dissociation of double-stranded DNA by small metal nanoparticles", Journal of Inorganic Biochemistry, 101(5): 824-30.*
Steven I. Dworetzky, Robert E. Lanford and Carl M. Feldherr ; "The Effects of Variations in the Number and Sequence of Targeting signals on Nuclear Uptake"; Published Oct. 1988; The journel of cell biology, vol. 107, Oct. 1988 1279-1287.
Alexander G. Tkachenko, Huan Xie, Donna Coleman, Wilhelm Glomm, Joseph Ryan, Miles F. Anderson, Stefan Franzen and Daniel L. Feldheim; "Multifunctional Gold Nanoparticle-Peptide Complexes for Nuclear Targeting"; Received Dec. 11, 2002; E-mail: Dan_Feldheim@NCSU.edu; Stefan_Franzen@NCSU.edu; 2 Pages.
Tamara V. Akhlynina, David A. Jans, Natalia V. Statsyuk, Irina Y. Balashova, Gabor Toth, Imre Pavo, Andrey A. Rosenkranz, Boris S. Naroditsky and Alexander S. Sobolev; "Adenoviruses Synergize With Nuclear Localization Signals to Enhance Nuclear Delivery and Photodynamic Action of Internalizable Conjugates Containing Chlorin e6"; Received Jun. 30, 1998; Revised Nov. 4, 1998; Int. J. Cancer: 81, 734-740 (1999).
F Zhang, P Andreassen, P Fender, E Geissler, J-F Hernandez and J Chroboczek; "A transfecting peptide derived from adenovirus fiber protein"; Received May 20, 1998; accepted Sep. 23, 1998; 11 Pages.
Guy Zuber, Liliane Zammut-Italiano, Emmanuel Dauty and Jean-Paul Behr; "Targeted Gene Delivery to Cancer Cells: Directed Assembly of Nanometric DNA Particles Coated with Folic Acid"; 2003 Wiley-VCH Verlag GmbH & Co. KGaA, Weinheim; DOI: 10.1002/anie.200250446; 4 Pages.
Sergei Svarovsky, Alexandre Borovkov and Kathryn Sykes; "Cationic gold microparticles for biolistic delivery of nucleic acids"; BioTechniques 45:535-540 (Nov. 2008) doi 10.2144/000112991; 5 Pages.
Alexander G. Tkachenko, Huan Xie, Yanli Liu, Donna Coleman, Joseph Ryan, Wilhelm R. Glamm, Mathew K. Shipton, Stefan Franzen and Daniel L. Feldheim; "Cellular Trajectories of Peptide-Modified Gold Particle Complexes: Comparison of Nuclear Localization Signals and Peptide Transduction Domains"; © 2004 American Chemical Society; Published on Web Apr. 28, 2004; 9 Pages.

\* cited by examiner

*Primary Examiner* — Robert M Kelly
(74) *Attorney, Agent, or Firm* — Fletcher Yoder, P.C.

(57) ABSTRACT

A nucleic acid-delivery vehicle for delivering nucleic acids to target cells is provided. The nucleic acid-delivery vehicle comprises a plurality of nanoparticles; and a plurality of nucleic acids. The nanoparticles and the nucleic acids are agglomerated to form a nucleic acid-granulation particle having a dimension of at least 5 nm. Methods of making the nucleic acid-delivery vehicle and kits comprising nucleic acid-delivery vehicle are also provided.

10 Claims, 3 Drawing Sheets

NUCLEIC ACID DELIVERY VEHICLE AND USES THEREOF

FIELD OF INVENTION

The invention generally relates to a nucleic acid-delivery vehicle, and methods for making the same. The invention specifically relates to nucleic acid-delivery vehicle comprising nucleic acid-granulation particles.

BACKGROUND

A variety of techniques are currently available for in vitro delivery of nucleic acids to cells and organelles, such as, transfection, microinjection, and electroporation. However, most of these techniques are not suitable for delivering nucleic acids or genes in vivo.

Receptor-mediated gene transfer is often used for introducing nucleic acids into suitable recipient cells, both in vitro and in vivo. This procedure involves attachment of nucleic acids to a ligand through a polycationic protein (usually poly-L-lysine), wherein the ligand is selected to target a specific receptor on the cell surface. Upon incubation with the recipient cells, the nucleic acids are delivered to the recipient cells through a receptor-mediated uptake mechanism. However, the expression level of the introduced transgene is dependent on several highly variable factors, such as, the stability of the nucleic acid-ligand complex, the presence and number of specific receptors on the recipient cell surface, or the receptor-ligand interaction.

As such, there is a need for a nucleic acid delivery vehicle that is stable enough to transfer sufficient amount of nucleic acids to the cells and a need for a consistent and reliable method for facilitating delivery of the vehicle. Although there exists a potential method that could be used for nucleic acid delivery to the cell, which is known as 'biolistic' nucleic acid delivery, this method does not reproducibly suited for existing protocols for preparing nucleic acid coated particles. The biolistic method is based on mechanical delivery of nucleic acid-coated particles into the cells or organelles using high-pressure-air propelled. Biolistic nucleic acid delivery is typically used for stable or transient transformation of nucleic acids to cells, and this delivery method is more suitable for delivery of plasmids and large nucleic acid fragments. Currently used nucleic acid-coated particles for biolistic delivery suffers from three disadvantages: 1) the amount of nucleic acids associated to each particle is less, and previous attempts to increase nucleic acids to each particle resulted aggregation of the particles; and 2) the loss of nucleic acids from the particles while the particles traverse through multiple layers of cells, and 3) the inability of the delivered nucleic acid to be localized into a cell, or into the nucleus of a cell. Thus, developing better nucleic acid-coated particles via more robust and reliable protocols is highly desirable.

BRIEF DESCRIPTION

The use of nanoparticles as delivery systems face challenges in terms of unresolved problems relating to the control, selection, and behavior of particle sizes, as well as problems surrounding the loading of particles with therapeutic agents, such as nucleic acids, proteins, peptides, or ligands. The design of a delivery vehicle of the present invention addresses these problems, which is a long-felt need in the art.

In one embodiment, a nucleic acid-delivery vehicle comprises a plurality of nanoparticles; and a plurality of nucleic acids. The nanoparticles and the nucleic acids are agglomerated to form a nucleic acid-granulation particle having a dimension of at least 5 nm.

In another embodiment, a method of making a nucleic acid-delivery vehicle, comprises providing a first solution comprising a plurality of nanoparticles and a second solution comprising a plurality of nucleic acids; mixing the first solution and the second solution to form a mixed solution; and dehydrating the mixed solution to generate a nucleic acid-granulation particle having a dimension of at least about 5 nm for making the nucleic acid-delivery vehicle.

In yet another embodiment, a kit for delivering nucleic acids to cells comprises a nucleic acid-delivery vehicle. The nucleic acid-delivery vehicle comprises a plurality of nanoparticles.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The invention is directed at nucleic acid-delivery vehicles, methods of making the nucleic acid-delivery vehicles, and kits for efficient delivery of nucleic acids into cells. The nucleic acid-delivery vehicle generally comprises a plurality of nanoparticles; and a plurality of nucleic acids. The use of the delivery vehicle, in part, enhances the efficiency of a nucleic acid transfection to the cells.

To more clearly and concisely describe and point out the subject matter of the claimed invention, the following definitions are provided for specific terms, which are used in the following description and the appended claims. Throughout the specification, use of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

As used herein, "nucleic acid-delivery vehicle" refers to a complex comprising a nucleic acid of interest that is used to efficiently deliver the nucleic acid of interest to one or more target cells.

As used herein, "agglomerate" refers to a non-covalent assembly of particles. The average size of the agglomerate generally ranges between about 20 nm and about 10 µm. Agglomeration is an act or process of gathering into a mass, whereby the particles collide due to the turbulence and adhere to or are associated with each other forming agglomerates. For example, nucleic acids and nanoparticles may be agglomerated upon dehydration of a solution comprising nucleic acids and nanoparticles.

As used herein, "nucleic acid-granulation particle" or "granulation particle" refers to a particle that is formed by agglomeration of nucleic acids and nanoparticles. Granulation is a commonly used method in which particulates and processing additives are combined to form an agglomerated particle, called granule, which comprises multiple individual particles. The granulation particles may have a homogeneous distribution. The granulation particle comprises nanoparticles and nucleic acids that are agglomerated into particles comprising multiple nanoparticles with a homogeneous distribution of nucleic acids. As a non-limiting example, the nucleic acids act as processing additives for the generation of granulation particle, whereby the granulation particle forms while a solution of nucleic acids and a solution of nanoparticles are mixed and then dehydrated or otherwise allowed to or forced to aggregate into clusters of particles each containing nucleic acid.

As used herein, "dimension" refers to the longest dimension of a nanoparticle or a granulation particle. For example, if the particle is spherical, the dimension is the diameter of the particle. For an elliptical particle, the dimension is the major axis of the ellipse. In hydrated forms, the dimension of a spherical particle may be the mean or average hydrodynamic diameter of the particle. Similarly, a granulation particle having a dimension of 1 micron (µm) refers to a granulation particle that has a longest dimension of at least 1 µm. For a granulation particle of irregular geometry, the size of the granulation particle may be described in terms of its dimension, the longest Euclidean distance between two points in the granulation particle.

As used herein, "nanoparticle" refers to particles, particle composites or hollow capsules having a dimension less than about 1000 nanometers (nm).

As used herein, "primer", or "primer sequence" refers to a short linear oligonucleotide that hybridizes to a target nucleic acid sequence (e.g., a deoxyribonucleic acid (DNA)) to prime a nucleic acid amplification reaction. The primer may be a ribonucleic acid (RNA) oligonucleotide, a DNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3-4 nucleotides long) do not form thermodynamically stable duplexes with target nucleic acids under such hybridization conditions. The upper limit is often determined by the possibility of having a duplex formation in a region other than the pre-determined nucleic acids sequences in the target nucleic acids. As a non-limiting example, suitable primer lengths are often in the range of about 4 to about 40 nucleotides long. A primer may also be used to capture a nucleic acid sequence.

As used herein, "plasmid" refers to an extra-chromosomal nucleic acid that is separated from a chromosomal nucleic acid. A plasmid DNA may be capable of replicating independently of the chromosomal nucleic acid (chromosomal DNA) in a cell.

As used herein, "biodegradable" means any structure, which decomposes or otherwise disintegrates after prolonged exposure to physiological conditions. To be biodegradable, the structure should be substantially disintegrated within a few weeks after introduction into the body. As a non-limiting example, brushite (calcium phosphate-nanoparticle) is a biodegradable nanoparticle material.

As used herein, "signal peptide" refers to a short peptide chain that directs the transport of a biologically active agent, attached to the peptide, to a target cell or organelle. The biologically active agent, for example, may be a peptide, protein, oligonucleotide, nucleic acid, ligand, or composition such as a pharmaceutical. As an example, the signal peptide is often 3-60 amino acids long. The amino acid sequences of the signal peptides, for example, may be used to direct the attached biologically active agent to certain organelles such as the nucleus, mitochondrial matrix, endoplasmic reticulum, chloroplast, and peroxisome. Some signal peptides may, in some examples, be cleaved from the biologically active agent by signal peptidase after the transport of biologically active agent.

As used herein, "nuclear localization signal" refers to an amino acid sequence, which directs a protein disposed in the cytoplasm of a cell across the nuclear membrane and into the nucleus of the cell. The nuclear localization signal may comprise amino acids in a range from about 4 to 25. In one non-limiting example, the signal comprises at least a four to eight amino acid sequence.

As used herein, "amplification product" refers to amplified nucleic acids that are generated by nucleic acid amplification from a nucleic acid template.

As used herein, "target nucleic acids" refer to nucleic acids that are required to introduce to a cell. For example, the target nucleic acids may be an RCA product comprising a tandem repeat nucleic acid sequence.

As used herein, "rolling circle amplification (RCA)" refers to a nucleic acid amplification reaction that amplifies a circular nucleic acid template (e.g., single stranded DNA circles) via a rolling circle mechanism. Rolling circle amplification reaction may be initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). Rolling circle amplification typically produces concatamers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatamers. For example, in a double-primed RCA, one primer may be complementary, as in the LRCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This may, in some cases, generate a discrete set of concatemeric, double-stranded nucleic acid amplification products. Rolling circle amplification may, for example, be performed in vitro under isothermal conditions using a suitable nucleic acid polymerase such as Phi29 DNA polymerase.

As used herein, "multiple displacement amplification" (MDA) refers to nucleic acid amplification, wherein the amplification comprises annealing a primer to a denatured nucleic acid followed by strand displacement nucleic acid synthesis. As the nucleic acid is displaced by strand displacement, a gradually increasing number of priming events occur, forming a network of hyper-branched nucleic acid structures. MDA is often employed for whole-genome amplification for generating high-molecular weight DNA with limited sequence bias from a small amount of genomic DNA sample. Strand displacing nucleic acid polymerases such as Phi29 DNA polymerase or large fragment of the Bst DNA polymerase may be used in multiple displacement amplification. MDA is usually performed under isothermal reaction conditions, and random primers are used in the reaction for achieving amplification with limited sequence bias.

As used herein, the term "nucleotide analogue" refers to compounds that are structurally similar (analogues) to naturally occurring nucleotides. The nucleotide analogue may have an altered phosphoate backbone, sugar moiety, nucleobase, or combinations thereof. Generally, nucleotide analogues with altered nucleobases confer, among other things, different base pairing and base stacking proprieties. Nucleotide analogues having altered phosphate-sugar backbone (e.g., Peptide Nucleic Acid (PNA), Locked Nucleic Acid (LNA)) often modify, among other things, the chain properties such as secondary structure formation.

As used herein, the term "LNA (Locked Nucleic Acid) nucleotide" refers to a nucleotide analogue, wherein the sugar moiety of the nucleotide comprises a bicyclic furanose unit locked in a ribonucleic acid (RNA)-mimicking sugar conformation. The structural change from a deoxyribonucleotide (or a ribonucleotide) to the LNA nucleotide is limited from a chemical perspective, namely the introduction of an additional linkage between carbon atoms at 2' position and 4' position (e.g., 2'-C, 4'-C-oxymethylene linkage. The 2' and 4' position of the furanose unit in the LNA nucleotide may be linked by an O-methylene (e.g., oxy-LNA: 2'-O, 4'-C-methylene-β-D-ribofuranosyl nucleotide), a S-methylene (thio-LNA), or a NH-mehtylene moiety (amino-LNA), and the like. Such linkages restrict the conformational freedom of the furanose ring. LNA oligonucleotides display enhanced hybridization affinity toward complementary single-stranded RNA, and complementary single- or double-stranded DNA. The LNA oligonucleotides may induce A-type (RNA-like) duplex conformations.

One or more embodiments are directed to a nucleic acid-delivery vehicle, which comprises a plurality of nucleic acids and a plurality of nanoparticles. The plurality of nucleic acids and nanoparticles are agglomerated to form a granulation particle.

In the nucleic acid-delivery vehicle, the nucleic acids are being packaged/condensed with nanoparticles to form a granulation particle. The granulation particle has a dimension in a range from about 5 nm to 1 μm. In some instances, the granulation particle may have a dimension greater than about 1 μm for some applications. The amount of nucleic acids associated with a defined amount of nanoparticles maybe increased without affecting the granulation particle formation. Nucleic acids are often retained in the nucleic acid delivery vehicle as the vehicle traverses through a series of layers, such as, the cell membrane or endosomal membrane before reaching the nucleus of the target cell.

While the delivery vehicle is designed to enter the cell, the nucleic acids may be designed to target a specific organelle within the cell. The nucleic acid delivery vehicle is stable enough to transfer a sufficient amount of nucleic acids to the cells. The granulation particles may be used for biolistic method of nucleic acid delivery. The biolistic method delivers nucleic acid-coated particles to the cells by a high-pressure blast. The granulation particles may have a dimension of nanometer to μm, which may be useful for biolistic delivery with high-pressure blast.

The nanoparticles and the nucleic acids are agglomerated to form a nucleic acid-granulation particle. The nucleic acids are captured within the agglomerated form of the granulation particle, which may improve the carrier capacity of the granulation particle. The granulation particles are composed of nanoparticle carriers for delivery of nucleic acids. The nanoparticles may be biocompatible. In one example, the nanoparticles may be biodegradable. The nanoparticles may comprise nucleic acids on their surface. The nucleic acids may be covalently attached to the nanoparticles and each of the nanoparticles may be non-covalently attached to other nanoparticles, while forming the granulation particle. The granulation particles may be fabricated to control their size, compressibility, and flowability, each of which may impact the processing stream for particle-mediated nucleic acid delivery.

The granulation particle may have different shapes and sizes. Non-limiting examples of the shapes of the granulation particles include but not limited to spherical, cubical, tetrahedral, octahedral, conical, or cylindrical. In one embodiment, the granulation particle is spherical in shape, wherein the average diameter of the particle is 1 μm. However, the smaller sized granulation particle may also be fabricated. For example, the granulation particle may be fabricated such that the dimension of the granulation particle is as small as about 5 nm. The dimension of the granulation particle ranges from about 5 nm to 10 μm. To optimize for biolistic nucleic acid delivery, the average dimension of the granulation particle is generally above 1 μm.

The nanoparticles used for the delivery vehicle may be solid particles or semi-solid colloidal particles. In some embodiments, the nanoparticles may be metal nanoparticles or non-metal nanoparticles. The nanoparticles may further be selected from metal oxide nanoparticles, metal nitride nanoparticles, metal carbides nanoparticles, and combinations thereof. For example, the metal nanoparticles may be selected from gold nanoparticles, silver nanoparticles, platinum nanoparticles, iron nanoparticles, iron oxide nanoparticles, titanium nanoparticles, $TiO_2$ nanoparticles, silica nanoparticles, alumina nanoparticles, zinc nanoparticles, zinc oxide nanoparticles, tin nanoparticles, tin oxide nanoparticles, copper nanoparticles, copper oxide nanoparticles, hafnium nanoparticles, hafnia nanoparticles, yttria nanoparticles, yttrium aluminum garnet nanoparticles, magnesium aluminate spinel nanoparticles, magnesium oxide nanoparticles, calcium carbonate nanoparticles, calcium phosphate nanoparticles or combinations thereof. The non-metal nanoparticles may comprise diamond nanoparticles.

The nanoparticles may also have various shapes and sizes. For example, but not necessarily, the nanoparticle metal component comprises an approximately spherical metal atom-comprising entity. The nanoparticle metal component may be, but is not limited to, an elemental metal or semiconductor material, such as a gold or $TiO_2$ nanoparticle. The nanoparticle may comprise super paramagnetic iron-oxide (SPIO) nanoparticle. SPIO's are small super-paramagnetic iron-oxide nanoparticle with a crystalline magnetite structure coated, for example, with dextran or a dextran derivative. The size of the nanoparticles may be in a range from about 0.5 nm to 1000 nm. The nanoparticles typically have an average diameter that less than 1000 nm.

The nanoparticle may be biocompatible and may be sufficiently resistant to chemical and/or physical destruction by the environment. For example, a sufficient amount of the nanoparticles may remain substantially intact after injection into the blood stream, given intra-peritoneally or orally or incubated with an in vitro sample. The nanoparticles may be a metallic nanoparticles, including, but not limited to, gold nanoparticles. The metal nanoparticles may be made of a pure metal or a metal composite.

The nucleic acid-delivery vehicle comprises nucleic acids, which may be single stranded or double stranded. It may comprise, for example but not limited to, 50 to 1,000,000 bases (or base pairs). In one or more of the examples, the nucleic acid sequences are between about 20 and 200 nucleotides in length.

In one embodiment, a nucleic acid sequence corresponding to a full-length gene, or a fragment thereof, may be used in the delivery vehicle. The bases may be the normal bases adenine (A), guanine (G), thymidine (T), cytosine (C) and uracil (U), or modified bases such as thiouracil, inosine, or 8-oxo-guanine. The nucleic acids may be deoxyribonucleic acids (DNAs), or ribonucleic acids (RNAs). The nucleic acids may comprise one or more nuclease resistant bases, nucleotide analogs, or synthetic nucleobases. The nucleic acids may be prepared using any suitable procedure. The DNAs may be selected from genomic DNAs, plasmid DNAs (e.g., purified/isolated plasmid DNA from a bacteriophage), synthetic DNAs, or amplified DNAs. The amplified DNAs or RNAs may be selected from polymerase chain reaction (PCR) products, rolling circle amplification (RCA) products, or multiple displacement amplification (MDA) products. In a specific embodiment, the amplified DNAs or RNAs are RCA products. The RCA product DNAs or RNAs often comprises tandem repeat sequences. Depending on the starting nucleic acid template, the amplified RCA product may also comprise one or more recombination sites.

The nucleic acid may comprise an expression cassette, which may comprise an expressible gene, which may express in a target cell. The expression cassette may comprise sequences such as promoter sequences and enhancer sequences if needed for the expression of the expressible gene in the target cell. The nucleic acids may comprise one or more nuclease-resistant bases, such as thioated bases. In some embodiments, the nucleic acids may code for an antigenic protein or polypeptide. As a non-limiting example, the nucleic acid delivery vehicle may be used as a nucleic acid-vaccine.

The delivery vehicle may comprise one or more bioactive materials along with nucleic acids, such as peptides, proteins, ligands, or compositions such as pharmaceuticals. In some embodiments, the granulation particles comprise signal peptides. The nanoparticles may be surface modified by localization signal peptides, such as, organelle specific receptor peptides or nuclear localization signals. The nuclear localization signals are utilized to enable effective localization of the delivered nucleic acids into the nucleus of cells for expression.

The signal peptides may be attached to the nanoparticles by covalent interactions. In one embodiment, the signal peptides are attached to all the nanoparticles present in granulation particle. In an alternative embodiment, the signal peptides may be attached to at least one nanoparticle present in the granulation particle. Some of the nanoparticles may comprise signal peptides; and some of the nanoparticles are devoid of signal peptides. The nanoparticles without signal peptides may be used to increase the mass of the granulation particle. In some embodiments, the signal peptides may be attached to the nucleic acids at the end of the nucleic acids. For example, the signal peptide may be attached to the 3'-end of the nucleic acids. In some embodiments, the signal peptide may be attached to 5'-end of the nucleic acids.

In some embodiments, the delivery vehicle may comprise one or more primers, attached to the nanoparticles. One or more primers may be attached to the surface of at least one nanoparticle. The primers may comprise signaling moiety attached to it. The primers may be random primers or specific primers. The primers may comprise a randomized sequence comprising modified nucleic acid bases. When universal random primers are used, the probability for capturing any target nucleic acids, by attachment to the primers, increases. While a specific nucleic acid sequence is desirable for nucleic acid delivery to the cells, specific primers may be used to capture the specific nucleic acid sequence, may be from a RCA amplification reaction. To avoid delivery of any non-specific nucleic acids to the cells, use of specific primers is beneficial. Therefore, depending on primer selection, the efficient delivery of nucleic acids to the cells can be ensured.

In some embodiments, the attached primers comprise a specific sequence. Suitable lengths of the primers may be in the range from about 4 to 30 nucleotides. In one embodiment, the specific primers attached to the nanoparticles may be used for capturing amplified nucleic acids from an amplification reaction medium and generate the granulation particle of the delivery vehicle. In a specific embodiment, the specific primers may be used for capturing amplified nucleic acids from RCA reaction medium to form granulation particles for delivery vehicle.

Granulation may be used to enhance nanoparticle processing, a route to combine nucleic acids and nanoparticles, and in some instances, as a means to generate a particle having a dimension of a µm, for instances in which such sizes are needed for particle-mediated nucleic acid delivery. While generating the granulation particle, nucleic acids are associated with the surface of the nanoparticles and the nucleic acids are trapped inside the granulation particle upon agglomeration. As the nucleic acids are embedded in the agglomerated mass, the possibility of inadvertently removing the nucleic acids from the granulation particle decreases. The nanoparticles remain sufficiently intact while entering into the cells. The biodegradation or solubilization of the nanoparticles is desirable only after entry into one or more targeted organelles of the cell, such as the nucleus.

One or more of the examples of the methods for making granulation particles, comprise, providing a first solution comprising a plurality of nanoparticles and a second solution comprising a plurality of nucleic acids, followed by mixing the first solution and the second solution to form a mixed solution; and dehydrating the dispersed mixed solution to generate a plurality of nucleic acid-granulation particles. In one embodiment, the granulation particle that is generated has a dimension of at least about 20 nm.

The dehydration of the mixed solution may be carried out by evaporation. The method of evaporation may be selected from spray drying granulation, wiped film evaporation, freeze dry granulation, fluid bed granulation or wet granulation.

In spray dry granulation, droplets of liquid (or mixed solution) are introduced into the top of a drying tube, and as they fall, liquid is evaporated yielding solid granules. In wiped film evaporation, liquid is wiped on a surface where droplets are uniformly dispersed and allowed to evaporate to dryness to create granules. During freeze dry granulation, droplets are introduced into liquid-nitrogen to freeze the droplets, and then frozen droplets are lyophilized to create dry granules. The fluid bed granulation involves suspending particulates in an air stream and spraying a liquid from the top down onto a fluidized bed. Particles in the path of the spray are slightly wetted and become sticky. The sticky particles are then collided with other particles, which adhere to each other to form a granule. In wet granulation, phase-separated droplets are created whereby one solvent slowly absorbs the other, leaving immiscible granules.

The nanoparticles may be produced by any suitable method, including, for example, emulsion polymerization in a continuous aqueous phase, emulsion polymerization in continuous organic phase, interfacial polymerization, solvent deposition, solvent evaporation, dissolution of an organic polymer solution, cross-linking of water-soluble polymers in an emulsion, dissolution of macro molecules, and carbohydrate cross-linking. These fabrication methods can be performed with a wide range of materials. Metal atoms, and structures comprising metal atoms, can also serve as effective nanoparticles. Nanoparticles may comprise a solid structure. Nanoparticles may comprise a hollow structure that may further contain a material inside. The nanoparticles may have a coating such as, but not limited to, metals or polymer coating materials.

The nucleic acid for targeting to cells or tissues, may be produced by a synthetic method or may be isolated from a source. The nucleic acids may be pre-amplified by any amplification method includes, but not limited to, PCR, RCA, or MDA. The natural or synthetic nucleic acids may be circular nucleic acids, nicked nucleic acids, or linear nucleic acids.

In one embodiment, a nucleic acid may be engineered to comprise a recombination site, and the engineered nucleic acid may be amplified to generate the amplified nucleic acid comprising the recombination sites. Engineering of the nucleic acid may be achieved by any of the genetic engineering or molecular biology techniques known in the art, such as, but not limited to, cloning. The nucleic acids may comprise a promoter sequence for expression of nucleic acids while entered in nucleus. It may further comprise a transcription initiator sequence and a transcription termination sequence. The targeted nucleic acids may comprise one or more recombination sites. The recombination sites comprise nucleic acid sequences that are favorable for recombination. In some embodiments, the recombination site may be a site-specific recombination site. The site-specific recombination site, in this example, refers to a recombination site comprising specific sequence, which is recognized by a specific recombination protein.

The nucleic acids may comprise DNAs and/or RNAs, or a DNA-RNA chimeric-forms. In some embodiments, the nucleic acids may be cDNA or genomic DNA. The circular nucleic acids may be synthetic (e.g., a linear or nicked DNA circularized by enzymatic/chemical reactions) or may be plasmid DNAs. The RNAs may be small RNA or small interfering RNA (siRNA). Small RNA is a class of double-stranded RNA molecules, 20-25 nucleotides in length, that play a variety of roles in the RNA interference (RNAi) pathway, where it interferes with the expression of a specific gene. The DNAs or RNAs may further comprise a signaling moiety attached to it. The signaling moiety may comprise a chromagenic compound, fluorogenic compound, or luminogenic compound, or a combination thereof. The signaling moiety may be a signal peptide. Non limiting examples of signal-generating moieties include enzymes, such as, horseradish peroxidase, alkaline phosphatase, acid phosphatase, glucose oxidase, beta-galactosidase, beta-glucuronidase or beta-lactamase; and fluorescent molecules, such as, fluoresceins, coumarins, BODIPY dyes, resorufins, and rhodamines.

The nucleic acids, for example, DNAs or RNAs may be collected from a donor. In one example, nucleic acids are collected from a donor, followed by amplification of the nucleic acids, and then captured on a nanoparticle for nucleic acid delivery to targeted cells or tissues. The nucleic acids may be amplified nucleic acids, which may be captured by employing nanoparticle-bound specific primers that are homologous to at least some part of the amplified nucleic acids sequences. The nanoparticle-bound specific primers may capture the amplified nucleic acids sequences, for example, by hybridizations.

In one embodiment, a single stranded nucleic acid sequence may be used instead of a double stranded nucleic acid sequence encapsulated in the granulation particles. When a sequence of a particular gene is known to be causative of a particular disease, a single strand of nucleic acid may synthesize and targeted to a cell. The single strand of nucleic acid may hybridize to the messenger RNA (mRNA) produced by that gene and inactivate or "silence" it, effectively turning that gene "off", as the mRNA has to be single stranded to be translated. For example, in RNA interference (RNAi), nucleic acids may be introduced to control gene-regulation. Two types of small RNA molecules, microRNA (miRNA) and small interfering RNA (siRNA), may be used in RNA interference. These small RNAs may bind to specific other RNAs and either increase or decrease their activity, for example, by preventing a messenger RNA from producing a protein.

Double stranded nucleic acids of various lengths and compositions are also suitable for use in the delivery vehicle. Double stranded nucleic acids comprising from about 10 base pairs to a full-length gene are useful in gene therapy applications. In one embodiment, the full-length genes can be incorporated into a host cell's genome or can be transiently expressed within the cell. For example, if a cell lacks a particular gene, an appropriate double stranded nucleic acid sequence may be incorporated into the cell to replace the functionality of the absent gene.

Nucleic acid analogs may also be used in the nucleic acid delivery vehicle. For example, peptide nucleic acid analogs (PNAs), locked nucleic acid analogs (LNAs), or morpholinos may be used. A peptide nucleic acid analog is a DNA analog, wherein the backbone of the analog, normally a sugar backbone in DNA, is a pseudopeptide. A PNA backbone may comprise a sequence of repeated N-(2-aminoethyl)-glycine units. Functionality of the PNAs may be the same as DNAs in a similar environment, and may additionally bind complementary nucleic acid sequences. In one aspect, PNAs offer a potential advantage over unmodified DNAs due to their ability to form stronger bonds and due to the neutrally charged peptide backbone of the analogs. The PNAs also impart a higher degree of specificity than is achievable by unmodified DNAs. PNAs have been employed in a wide array of biochemical roles, such as, sequence mapping. For example, in vitro studies indicate that PNA may be used to inhibit both transcription and translation of genes to which it has been engineered with a complementary sequences that PNAs may be useful in antigene and antisense therapy. Another nucleic acid analog is morpholinos. They are known as antisense oligos, which are used to modify gene expression. Morpholino oligomers (oligos) are used in antisense technology to block other molecules from accessing specific sequences within the nucleic acid. Morpholinos block small (~25 base) regions of the base-pairing surfaces of ribonucleic acid (RNA).

The nucleic acids or other bioactive materials may be attached to the nanoparticles through one or more linkers. A linker may comprise, for example, an oligonucleotide, a peptide, a polymeric chain, or an affinity tag. In one embodiment, the linker may be oligonucleotides, such as specific primers. The specific primer may be attached to the nanoparticles via covalent linkage, electrostatic interaction, Van der Waals interactions, hydrophobic interaction, or a combination of these. For example, the specific primers may be covalently attached to one or more nanoparticles. The specific primers may further be attached to the nanoparticles either directly or via a linker. In one non-limiting embodiment, the linker may be a polymer, such as acrylamide, dextran, or poly ethylene glycol (PEG). In at least one embodiment, one end of a linker may comprise a reactive group (such as an amide group), which forms a covalent bond with the specific primer to be immobilized.

In one or more embodiments, covalent chemical attachment of a specific primer sequence to the nanoparticle may be accomplished by using standard coupling agents. For example, water-soluble carbodiimide may be used to link the 5'-phosphate of a specific primers sequence to amine-coated nanoparticle through a phosphoamidate bond. Other linkage chemistries, that may be used to join the oligonucleotide to the nanoparticles, include, but are not limited to, N-hydroxysuccinamide (NHS) and its derivatives.

The delivery vehicle may comprise at least two components, such as nanoparticles and nucleic acids. In another embodiment, the delivery vehicle of the present invention may comprise at least three components, such as nanoparticles, one or more signal peptides (such as nuclear localization signals) and nucleic acids. These three components may be prepared and assembled together to function as a delivery vehicle, which may be targeted for delivery to the nucleus of a cell via a nuclear localization signal. Nucleic acids and nuclear localization signals may be synthesized using primers or templates previously associated with the nanoparticles. The nuclear localization signal directs the translocation of the delivery vehicle to the nucleus of a cell, whereupon the nucleic acids can interact, for example, with one or more proteins or nucleic acids to facilitate a desired effect.

A non-limiting representative nuclear localization signal is a peptide sequence that directs the protein to the nucleus of the cell in which the sequence is expressed. A nuclear localization signal is predominantly basic and can be positioned almost anywhere in a protein's amino acid sequence. Generally, the nuclear localization signal comprises a short sequence of four amino acids to eight amino acids, and may be rich in lysine and arginine residues. Nuclear localization signals often comprise proline residues. A variety of nuclear localization signals are available and have been used to effect transport of biological molecules from the cytoplasm to the nucleus of a cell. Translocation may be through the nuclear pore proteins.

In one embodiment, a nuclear localization signal is attached to the nanoparticle. The nuclear localization signal may be synthesized or excised from a larger sequence. As noted, a variety of nuclear localization signals are available and selection of an appropriate sequence may be made based on the known properties of these various sequences. Nuclear localization signals may appear at various points in the amino acid sequences of proteins. Nuclear localization signals may be at the N-terminus, the C-terminus or in the central region of proteins. Thus, a selected sequence may serve as the functional component of a longer peptide sequence. Although there are no limits on the composition of a nuclear localization signal-comprising sequence, such a sequence may be functionally limited in length and composition, depending on a given application.

A suitable nuclear localization signal, attached to the granulation particle, may be synthesized or isolated. For example, nuclear localization signals may be synthesized using standard peptide chemistry techniques or may be isolated by proteolytic cleavage from a larger protein. Isolated or synthesized nuclear localization signals may be of any size, and the sequence should comprises at least a known nuclear localization signals which, for example, may be four to eight amino acids in length. Protein and peptide purification methods suitable for preparing nuclear localization signals, which are isolated from larger proteins, are known in the art.

The chemistry of attaching proteins and peptides to nanoparticles (e.g. gold nanoparticle) may be carried out using a thiol reaction. The reaction may involve a thiol group disposed on the nuclear localization signal, which may take the form of a terminal cysteine or methionine residue, or on the nanoparticle. The thiol group may be reacted with a primary amine on the alternate entity. The primary amine may conveniently take the form of a terminal lysine or arginine residue in the nuclear localization signal, but may also be disposed on the surface of the nanoparticle.

A plurality of signal peptide sequences may be associated with a nanoparticle delivery vehicle. Various sequences, such as receptor mediated endocytosis (RME) sequences, may also be associated with a delivery vehicle. These additional sequences may aid in the translocation of a vehicle across various membranes, such as the nuclear membrane of a cell or the endoplasmic reticulum (ER) membrane of a cell. Thus, for membranes and other structures that generally inhibit translocation of a vehicle to a given location in a cell, NLS and RME sequences may be used to enable a given nanoparticle delivery vehicle to pass through various potential barriers for translocation and target a variety of different cell types. For example, the gold and SPIO nanoparticles may be surface modified using standard attachment chemistry, e.g., thiol chemistry, NHS-ester chemistry; to conjugate different localization peptides, e.g., TAT-PTD, SAP, sv-40 NLS, or adeno-NLS.

A suitable method for efficient delivery of the nucleic acids into the cells includes, but it is not limited to, electroporation, ultrasound mediated DNA delivery, magnetic field induced delivery, optically induced delivery, and biolistic delivery. Typically, gene-gun delivery requires a burst of air that carries small micro particles coated with nucleic acids, to the cell/tissue of interest. Generally, μm-sized nucleic acid granulation particle is particularly suitable for this type of nucleic acid delivery. For example, when the tissue or organ of interest is skin, the mass of the micro particle helps to carry the nucleic acids through the outer layer of skin cells into the living cells present underneath the stratum corneum.

The localization and the effect of delivery may be used to track using various signal peptides or proteins. The cellular or sub-cellular localization and the effect of nucleic acid-delivery may be identified by transmission electron microscopy, Raman microscopy, confocal microscopy or other analytical techniques for determining the concentration and localization of the active nanoparticles in the cell. One or more appropriate proteins may further be localized on the surface of the particle. The appropriate proteins may comprise, for example, ligases, restriction enzymes or other DNA processing enzymes. For example, a recognition moiety (signal peptide or protein) may comprise a sequence that is subject to enzymatic or electrochemical cleavage. The recognition moiety may thus comprise a sequence that is susceptible to cleavage by enzymes present at various locations inside a cell, such as proteases or restriction endonucleases (e.g. DNAse or RNAse).

The nucleic acid-delivery vehicles of the invention may be used, for example, in DNA vaccines, gene therapy, modulation of gene expression, altering RNA splicing and/or modulation of protein-protein interactions. The delivery of the nucleic acids may be accomplished in the same cellular or tissue location, or in two or more different cellular or tissue locations, depending on the targeting sequences that are employed.

The nucleic acid-delivery vehicle may be used in a variety of subjects including warm-blooded animals, such mammals, including, for example, humans, dogs, cats or other small animals. Additionally, the delivery vehicle may be used with prokaryotic and eukaryotic microorganisms or with in vitro cultures. The nanoparticle delivery vehicle of the invention may be used as a diagnostic agent in all of the above subjects, as well as a therapeutic agent.

The target nucleic acids may be delivered to the cells in the form of a nucleic acid-vaccine, for example, a DNA-vaccine. A safe and effective vaccine composition against a virus may comprise an effective immunizing amount of an immunogenically active component. For example, an antigen derived from the virus, a nucleic acid derived from the virus, a plasmid DNA of the virus, a plasmid with sequence inserts of the virus, and a mixture thereof. It may also comprise an immunogenically stimulating amount of an adjuvant, and a pharmacologically acceptable carrier may be administered to mammals, to prevent the disease caused by said virus. The term, "immunogenically active" designates the ability to stimulate an immune response, i.e., to stimulate the production of antibodies, particularly humoral antibodies, or to stimulate a cell-mediated response. For example, the ability to stimulate the production of circulating or secretory antibodies or the production of a cell-mediated response in local mucosal regions, (e.g., intestinal mucosa), peripheral blood, cerebral spinal fluid or the like.

The effective immunizing amount of the immunogenically active component may vary and may be any amount sufficient to evoke an immune response and provide immunological protection against a specific pathogen causing disease. The immunogenicity of nucleic acid vaccines is directly linked to cell transfection efficiency and the level of antigenic expression of proteins after delivery of nucleic acids and subsequent protein expression. The nucleic acids that are selected from RCA product increases gene expression in cells. Increasing either the amount of nucleic acids or the stability of the nucleic acids may induce higher level of expression of nucleic acids in cells.

In some embodiments of the kit of the invention for delivery of nucleic acids comprises a nucleic acid-delivery vehicle comprising a plurality of nanoparticles, wherein the nanoparticles comprise one or more specific primers attached to the nanoparticles. The specific primers may comprise a sequence, which is homologus to the nucleic acid sequence for delivery. In one embodiment, the specific primers may be used to capture amplified nucleic acids produced by RCA reaction. The captured nucleic acids can be delivered by nucleic acid-delivery vehicle to target cells or tissues.

In some embodiments of the kit, the nanoparticles may further comprise one or more signal peptides attached to the nanoparticles for localization of nucleic acids to cells, and cell-organelle. The kit may further comprise reagents or reagent solutions required for performing the nucleic acid delivery. It may further comprise an instruction manual detailing the specific components included in the kit, or the methods for using them in nucleic acid delivery, or both.

Example 1

Preparation of Super Coiled DNA and RCA DNA

Plasmid DNAs encoding influenza hemagglutinin (HA), nucleoprotein (NP), or green fluorescent protein (GFP) were used for studying DNA expression in various cells by using nucleic acid-delivery vehicle comprising granulation particles. Influenza plasmids were used as well-established model antigens for antibody and T cell immunogenicity studies in mice. The GFP plasmids were used for expression studies in vitro and as a negative control for in vivo immunogenicity studies. Control supercoiled DNA formulations were prepared by standard methods using an endotoxin-free maxiprep plasmid kit from Qiagen.

The target DNA was amplified by RCA reaction. Minimal circular DNA for expression was used as template for RCA reactions as follows: the expression plasmid DNA was subjected to restriction digestion with the appropriate enzymes to eliminate all non-essential elements, followed by gel purification of the digested product, and finally self ligated to form the minimal circle needed for expression of a gene of interest (e.g., a foreign gene). Standard RCA reactions and those with varying levels of phosphorothioated nucleotides were used to generate the different RCA DNA products from the different template circles.

Standard RCA reactions involve the use of an initial circular template DNA, typically a 1-2 ng of supercoiled plasmid DNA or relaxed circular DNA that was created by self-ligation of a linear DNA fragment. For the nucleic acid amplification reaction, the primer-nucleotide mixed solution and an enzyme solution containing DNA polymerase were mixed together with template nucleic acid to create an amplification reaction, which was then incubated at about 30° C. The isothermal amplification reaction was performed in presence of input template plasmid DNA, Phi 29 DNA polymerase in presence of random primer, and optionally a nanoparticle-bound specific primer, and plasmid DNA. Over the course of a few hours, an exponential cascading amplification reaction produced amplified DNA. Typical reactions provide about a $10^6$- to $10^7$-fold amplification of the template DNA (ng of template to milligrams of product).

DNA amplification reactions were performed by incubating the primer-nucleotide mixed solution and the enzyme solution at 30° C. for about 400 min with plasmid DNA template. The amplification reaction mixture was composed of 40 µM random primer; and optionally 1 µM specific primer-conjugated nanoparticle; 400 µM dNTPs (400 µM each of dATP, dCTP, dGTP, dTTP); 1 pg plasmid DNA, and 200 ng phi29 DNA polymerase (200 ng per 10 µL reaction).

The reaction mixture was incubated at 30° C. in 50 mM HEPES buffer (pH=8.0) containing 15 mM KCl, 20 mM $MgCl_2$, 0.01% (v/v) Tween-20, 1 mM TCEP.

Substitution of nucleotides with thiophosphorylated nucleotides demonstrated that thiophosphorylated nucleotides were well tolerated in the RCA reaction. The resulting partially thioated RCA DNA was also capable of supporting protein expression when examined in vivo. The protein expression indicates that this nucleotide substitution was capable of being recognized and used by the cellular components required for transcription. This nucleotide analog inhibits DNA degradation by exonuclease action.

Example 2

Generation of RCA Product DNA-SPIO Granulation Particles

Figure 1:
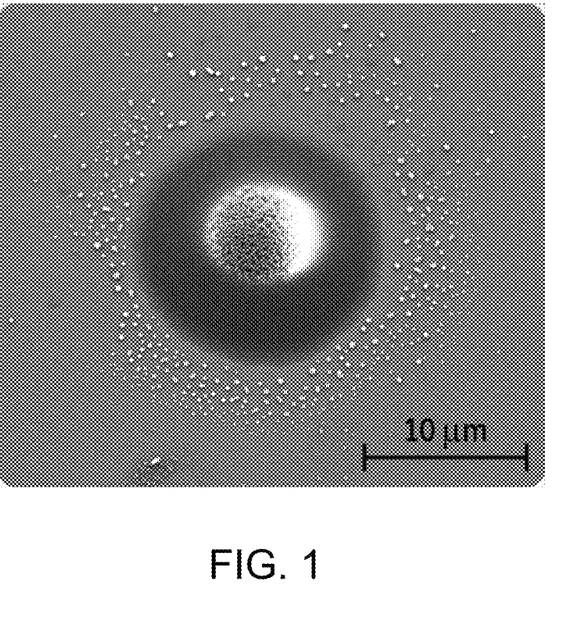
FIG. 1 is a scanning electron microscope (SEM) image of an example of a granulation particle of the invention using iron oxide nanoparticles and deoxyribonucleic acids.

The granulation particles having desired size (dimension) and composition were prepared by employing solvent extraction. A 260 μg/ml solution of RCA product DNA and different amounts of aqueous solutions of $10^{15}$ particles/ml of super paramagnetic iron oxide (SPIO) particles having dimension of 5 nm were mixed together to form a mixed solution. A plurality of approximately 0.3 μl droplets of this mixed solution was then added to n-butanol-chloroform (butanol:chloroform=5:2 ratio, density=1 g/ml) solution with constant mixing to allow for solvent extraction of the water from the SPIO-RCA DNA mixture droplets. After about 10 minutes, the liquid (mixed solution) in each droplet was absorbed by the solvent-solution (organic solution), leaving small agglomerates or granulation particles, in the range of 1 μm to 10 μm of dimension (FIG. 1). A large-scale preparation of granulation particles in the expected dimension composed of DNA and nanoparticles could also be produced by this method.

Figure 2:
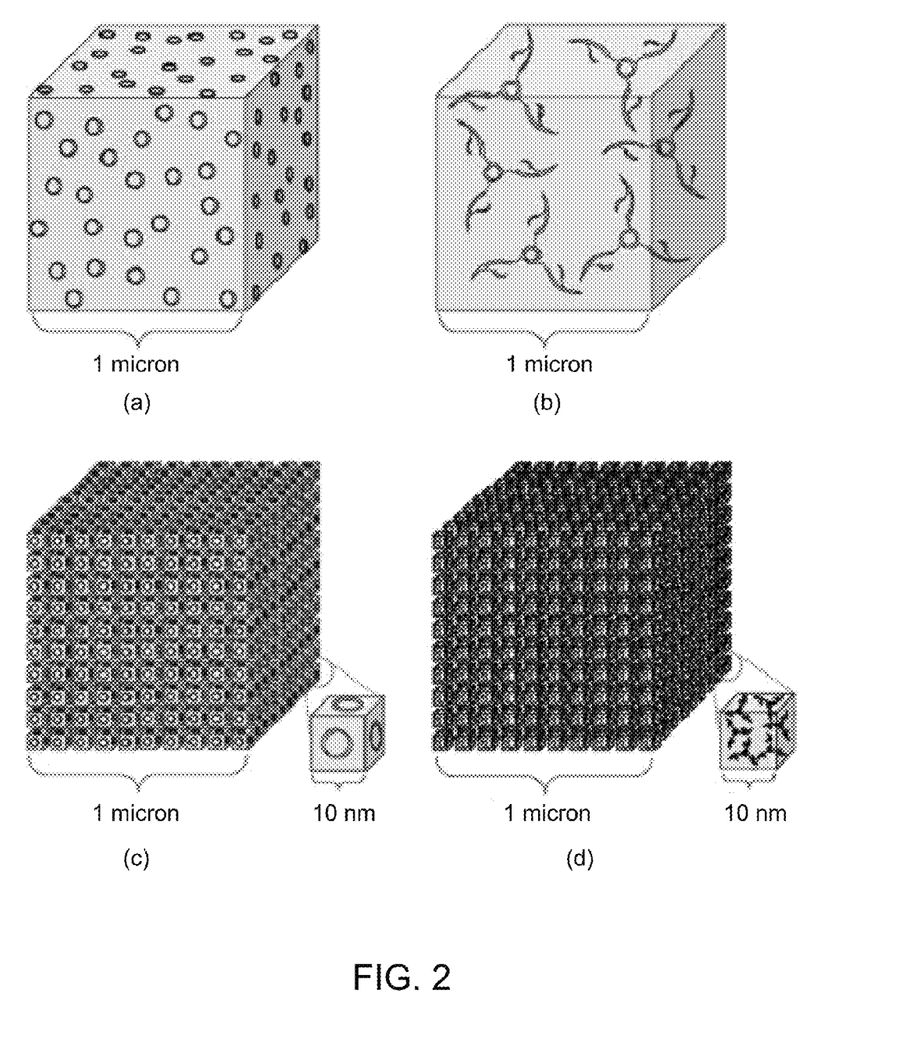
FIGS. 2a through 2d are perspective drawings of examples of the illustrative structure of granulation particles comprising nanoparticles and deoxyribonucleic acids before evaporation (FIGS. 2a, 2b, respectively) and after evaporation (FIGS. 2c, 2d, respectively) of solvent.
Figure 3:
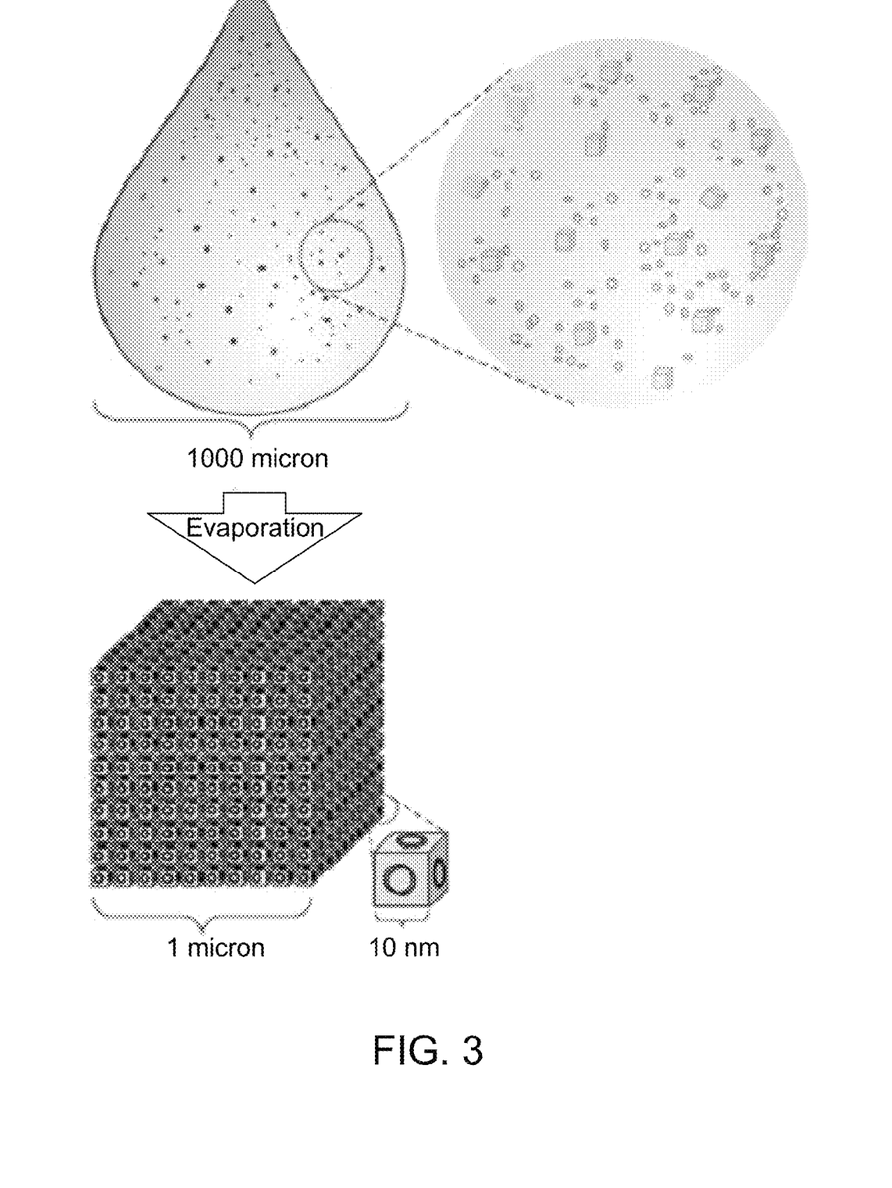
FIG. 3 is a schematic drawing of an example of the method for making agglomerated nucleic acid-granulation particles comprising nanoparticles and deoxyribonucleic acids after evaporation from a solution droplet.

Different amounts of supercoiled DNA were used for granulation using standard supercoiled plasmid DNA as shown in FIGS. 2 (a-d). Solvent-base granulation was initially used. Another method of granulation is thin film evaporation or spray dry granulation, which may provide an easier and more controllable method of granulation. SEM and light microscopy were used to determine the particle size. Particle size was specified by the concentration of nanoparticles used during the procedure. Increasing the concentration of nanoparticles in each small droplet would result in more nanoparticles per granulation particle, thereby increasing the size of the granulation particle.

Biocompatible materials can be included in this formulation to aid in mechanical stability or other property. For example, sugars such as sucrose, fructose or melizotose, macromolecules such as poly ethylene glycol, inulin, ficol or dextran, and proteins such as albumin can be used. The resulting particles can be solublized in aqueous environments.

Example 3

Precipitation of DNA on Micro Particles

DNA coated gold nanoparticles were prepared by a well-established spermidine-ethanol precipitation protocol. DNA was selected from various sources, such as super coiled DNA, rolling circle amplification DNA (RCA DNA), and thioated RCA DNA (tRCA DNA). Each DNA formulation was precipitated on to 25 mg of 1 μm gold particles. The precipitation reaction used was as follows: The gold was suspended in 50 mM spermidine followed by sequential additions of 25 to 250 μg of DNA and 10% $CaCl_2$. After 10 minutes, the gold-DNA complex was collected by a brief microfuge spin and washed three times with absolute ethanol to remove excess precipitation reagents. The gold-DNA was then suspended in 100% ethanol and loaded into a tube turner that coats the inside of a tefzel tube with the gold-DNA. The coated tube was dried and cut into 0.5 inch cartridges that were loaded into a gene gun prior to use. To maximize the DNA-gold loading rate, increasing amounts were added to the mixture up to a maximum threshold that coats the DNA onto individual gold particles without clumping.

Example 4

Analysis of Nucleic Acid Loading Efficiency

Preparation of granulation particles with plasmid DNA or RCA DNA and gold beads could yield a homogeneous composition of the resulting particles. DNA loading efficiency for various DNA could be determined, using purified plasmid DNA and RCA DNA, which were stained with SYBR gold (Life Technologies) in which a small amount of the intercalating dye (1:1,000 dilution) was included in the DNA mixture to pre-label the DNA for later fluorescent analysis. Gene gun cartridge is formulated with YOYO-1 stained DNA and is fired at 200 psi into water agar plates. The agar plates are then imaged and analyzed for spot intensity using fluorescent imaging. Analysis of DNA using this procedure would demonstrate significant amount of DNA is associated with each particle.

Example 5

Particle Barrier Penetration Assay

Successful delivery of nucleic acid-delivery vehicle by particle-mediated delivery to a skin tissue required penetration of the dead cells of stratum corneum. To determine the effect of barrier penetration, which might influence the amount of RCA or supercoiled DNA to deliver by the gene gun, an in vitro particle barrier penetration assay is performed.

Each RCA DNA or supercoiled plasmid DNA of granulation particles is stained with SYBR gold, and then particles are fired with the gene gun through 1 to 3 layers of clear mylar sheets laid over the water agar plates. Mylar sheets are used as a representative barrier with penetration resistance that found to be similar to the stratum corneum of skin in swine. A single mylar sheet is routinely used as a control for the final cartridge formulations. The fluorescence intensity of individual particle is analyzed following delivery of the particles. The result showed that over 50% of the DNA is stripped off from the gold micro particle (where DNA was precipitated on the 1 μm gold particle) during barrier penetration. The similar experiment with granulation particle is demonstrated that a lower amount of DNA is stripped off from the granulation particle after barrier penetration.

Example 6

Analysis of the Effect of Various DNA Formulations on Gene-Gun Cell Transfection In Vitro Flow cytometry was used to determine the effects of each DNA formulation for gene expression in cells. The granulation particles were introduced into cells wherein, the granulation particles comprising gold nanoparticles and DNA. The granulation particles were introduced to the cells by in vitro transfection using gene gun. Purified plasmid DNA and RCA DNA encoding green fluorescence proteins (GFP) were stained with TOTO-3 according to manufacturer's instructions (Life Technologies). A standard laboratory tissue culture strain, Vero cells, are suspended in liquid media and then transfected with TOTO-3-labeled GFP coding DNAs by particle-mediated delivery. The transfection by particle-mediated delivery is carried out by placing a pellet of the cells on a sterile sheet of parafilm, and coving the mass of cells with a single layer of mylar sheet. A gene gun cartridge loaded with the granulation particles and is discharged at 200 psi through the mylar sheet into the cell mass. Immediately following gene gun transfection, the cells were re-suspended in media, incubated for 5 hours and then analyzed by flow cytometry to determine the percentage of cells that received granulation particles. By flow cytometry, the GFP expression was also analyzed to determine the percentage of cells that received granulation particles that express the DNA.

Example 7

Analysis of Duration for Protein Expression in Intact Skin

To determine in vivo gene gun delivery of the different DNA formulations for production or duration of antigenic expression in the skin, granulation particles are made with RCA DNA and supercoiled GFP plasmid DNA. The granulation particles are delivered by gene gun into skin of mice. RCA and supercoiled NP-coding plasmids are also used as negative controls. The DNA-coated gold particles are delivered by gene gun into the epidermal skin layer as known in the art. Following delivery, GFP expression is visualized on the abdomen of anesthetized mice, imaged, and quantified daily for 10 days using a fluorescent dissection scope to compare both the amount and the duration of protein expression.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A nucleic acid-delivery vehicle comprising:
a plurality of nanoparticles; and
a plurality of double-stranded nucleic acids, wherein the nanoparticles and the double-stranded nucleic acids are agglomerated to form a nucleic acid-granulation particle, wherein the longest dimension of the nucleic acid granulation particle is at least 5 nm wherein the granulation particle comprises the plurality of nanoparticles with a homogenous distribution of the double-stranded nucleic acids, and wherein the granulation particles comprise a mix of nanoparticles with covalently attached signal moieties and nanoparticles devoid of signal moieties.

2. The nucleic acid-delivery vehicle of claim 1, wherein the longest dimension is in a range from about 5 nm to 10 µm.

3. The nucleic acid-delivery vehicle of claim 1, wherein the nanoparticles are selected from metal nanoparticles, metal oxide nanoparticles, metal nitride nanoparticles, metal carbides nanoparticles, and combinations thereof.

4. The nucleic acid-delivery vehicle of claim 1, wherein the nanoparticles are selected from gold nanoparticles, iron nanoparticles, iron oxide nanoparticles, titanium nanoparticles, titanium oxide nanoparticles, silica nanoparticles, alumina nanoparticles, zinc nanoparticles, zinc oxide nanoparticles, tin nanoparticles, tin oxide nanoparticles, copper nanoparticles, copper oxide nanoparticles, hafnium nanoparticles, hafnia nanoparticles, yttria nanoparticles, yttrium aluminum garnet nanoparticles, magnesium aluminate spinel nanoparticles, magnesium oxide nanoparticles, calcium carbonate nanoparticles, calcium phosphate nanoparticles, diamond nanoparticles, silver nanoparticles, and platinum nanoparticles.

5. The nucleic acid-delivery vehicle of claim 1, wherein the nanoparticles comprise one or more specific primers attached to the nanoparticles.

6. The nucleic acid-delivery vehicle of claim 1, wherein the nucleic acids are deoxyribonucleic acids or ribonucleic acids.

7. The nucleic acid-delivery vehicle of claim 1, wherein the nucleic acids comprise one or more nuclease-resistant bases or nucleotide analogs.

8. The nucleic acid-delivery vehicle of claim 1, wherein the nucleic acids code for an antigenic polypeptide, or a protein.

9. A deoxyribonucleic acid vaccine comprising the nucleic acid-delivery vehicle of claim 8, wherein the nucleic acids are deoxyribonucleic acids.

10. A nucleic acid-delivery vehicle comprising:
a plurality of nanoparticles; and
a plurality of double stranded nucleic acids, wherein the nanoparticles and the double stranded nucleic acids are agglomerated to form a double stranded nucleic acid-granulation particle having a longest dimension of at least 5 nm and wherein the double stranded nucleic acid-granulation particle comprises nucleic acids that are only double stranded.

* * * * *